(12) United States Patent
Morinaga (10) Patent No.: US 9,075,782 B2
(45) Date of Patent: Jul. 7, 2015

(54) MASS SPECTROMETRY DATA ANALYSIS METHOD AND ANALYSIS DEVICE

(75) Inventor: Hiroko Morinaga, Kyotanabe (JP)

(73) Assignee: SHIMADZU CORPORATION, Kyoto (JP)

( * ) Notice: Subject to any disclaimer, the term of this patent is extended or adjusted under 35 U.S.C. 154(b) by 529 days.

(21) Appl. No.: 13/458,721

(22) Filed: Apr. 27, 2012

(65) Prior Publication Data

US 2012/0303288 A1    Nov. 29, 2012

(30) Foreign Application Priority Data

May 25, 2011 (JP) ................................. 2011-116601

(51) Int. Cl.
  *G06F 19/00*  (2011.01)
  *G06F 19/24*  (2011.01)
(52) U.S. Cl.
  CPC ...................................... *G06F 19/24* (2013.01)
(58) Field of Classification Search
  CPC ............ G01N 23/207; G01N 23/2076; G01N 27/622; G06F 17/3007; G06F 19/00; G06F 19/24
  USPC ............................................ 702/23, 124–126
  See application file for complete search history.

(56) References Cited

U.S. PATENT DOCUMENTS

| 6,675,104 | B2 * | 1/2004 | Paulse et al. ..................... 702/22 |
| 2010/0116981 | A1 * | 5/2010 | Kajihara ........................ 250/282 |
| 2013/0158882 | A1 | 6/2013 | Komatsu et al. | |

FOREIGN PATENT DOCUMENTS

| JP | 2004-271185 A | 9/2004 |
| JP | 2005-221250 A | 8/2005 |
| JP | 2006-284305 A | 10/2006 |
| JP | 2010-261939 A | 11/2010 |
| WO | 2008/126151 A1 | 10/2008 |

OTHER PUBLICATIONS

Kiyoshi Ogawa, et al., "Research and Development of Mass Microscope," Shimadzu Review, Jan. 2006, pp. 125-135, vol. 62, No. 3-4.
Japanese Office Action issued Jul. 1, 2014 in Japanese Patent Application No. 2011-116601.

* cited by examiner

*Primary Examiner* — Phuong Huynh
(74) *Attorney, Agent, or Firm* — Sughrue Mion, PLLC (57) ABSTRACT

A data matrix in which pixel numbers are assigned to the vertical direction, m/z values are assigned to the horizontal direction, and intensity values are used as terms is generated from data obtained by peak detection (S3), and after the standardization of the data is executed so that the norms of the intensities of the pixel space are set to 1 for each m/z, the peaks (m/z values) are classified into a plurality of clusters by performing clustering in the m/z direction (S5 and S6). Since the probability of isotope peaks or adduct ion peaks derived from the same substance being consolidated into the same cluster increases, unnecessary peaks can be accurately removed by removing unnecessary isotope ion peaks and the like using m/z differences or intensities in the clusters (S7 and S8).

6 Claims, 11 Drawing Sheets

(4 of 11 Drawing Sheet(s) Filed in Color)

| | M₁ | M₂ | M₃ | --- | Mₙ |
|---|---|---|---|---|---|
| 1 | P₁₁ | P₁₂ | P₁₃ | --- | P₁ₙ |
| 2 | P₂₁ | P₂₂ | P₂₃ | --- | P₂ₙ |
| 3 | P₃₁ | P₃₂ | P₃₃ | --- | P₃ₙ |
| 4 | P₄₁ | P₄₂ | P₄₃ | --- | P₄ₙ |
| 5 | P₅₁ | P₅₂ | P₅₃ | --- | P₅ₙ |
| ⋮ | ⋮ | ⋮ | ⋮ | ⋱ | ⋮ |
| m | Pₘ₁ | Pₘ₂ | Pₘ₃ | --- | Pₘₙ | m/z →, PIXELS ↓

NORMS: | Q₁ | Q₂ | Q₃ | --- | Qₙ |

(b)

| | M₁ | M₂ | M₃ | --- | Mₙ |
|---|---|---|---|---|---|
| 1 | P₁₁/Q₁ | P₁₂/Q₂ | P₁₃/Q₃ | --- | P₁ₙ/Qₙ |
| 2 | P₂₁/Q₁ | P₂₂/Q₂ | P₂₃/Q₃ | --- | P₂ₙ/Qₙ |
| 3 | P₃₁/Q₁ | P₃₂/Q₂ | P₃₃/Q₃ | --- | P₃ₙ/Qₙ |
| 4 | P₄₁/Q₁ | P₄₂/Q₂ | P₄₃/Q₃ | --- | P₄ₙ/Qₙ |
| 5 | P₅₁/Q₁ | P₅₂/Q₂ | P₅₃/Q₃ | --- | P₅ₙ/Qₙ |
| ⋮ | ⋮ | ⋮ | ⋮ | ⋱ | ⋮ |
| m | Pₘ₁/Q₁ | Pₘ₂/Q₂ | Pₘ₃/Q₃ | --- | Pₘₙ/Qₙ |

NORMS: | 1 | 1 | 1 | --- | 1 |

FIG. 6

| | PC | $[M+H]^+$ | $[M+Na]^+$ | $[M+K]^+$ |
|---|---|---|---|---|
| ■ | C32:0 | 734.6 | 756.6 | 772.6 |
| ● | C34:1 | 760.6 | 782.6 | 798.6 |
| ▲ | C36:1 | 788.6 | 810.6 | 826.6 |
| ○ | C38:6 | 806.6 | 828.6 | 844.6 |
| □ | C40:6 | 834.6 | 856.6 | 872.6 |

| HC# | | | | | | | | | | |
|---|---|---|---|---|---|---|---|---|---|---|
| 1 | 546.1 | 562.1 | 567.9 | 568.9 | 569.9 | 581.1 | 585.1 | 601.0 | 624.0 | 625.0 |
| 2 | 626.0 | 627.0 | | 632.0 | 633.0 | | | | | |
| 3 | 545.1 | 580.1 | 716.1 | | | 717.1 | 761.0 | 852.1 | | |
| 4 | ■734.6 | ●760.6 | ○806.6 | □834.6 | | | | | | |
|   | 527.0 | 575.5 | 577.5 | 579.0 | 592.1 | | 603.5 | 607.0 | 613.2 | 651.5 |
|   | 675.1 | 677.0 | 682.0 | 698.0 | 700.0 | 703.6 | 719.0 | 732.5 | 735.6 | ■756.5 |
|   | 758.5 | 761.8 | 762.6 | ■772.5 | ●782.6 | 783.5 | 784.6 | 786.6 | 787.6 | ▲788.6 |
|   | 789.6 | ●798.5 | 799.5 | 800.5 | 807.6 | 808.6 | ▲810.6 | 817.1 | ▲826.5 | ○828.6 |
|   | 829.5 | 830.5 | 832.5 | 835.6 | 836.6 | ○844.5 | 853.1 | □856.6 | 857.6 | 868.6 |
|   | 870.6 | 871.6 | □872.5 | 886.8 | 891.8 | 893.7 | 895.6 | 896.6 | 897.6 | 898.6 |
|   | 899.6 | 914.7 | 918.6 | 919.6 | 920.6 | 921.7 | 922.6 | 923.7 | 924.6 | 925.8 |
|   | 942.6 | 943.6 | 970.6 | 971.6 | 972.6 | | | | | |

| HC# | | | | | | | | | | | |
|---|---|---|---|---|---|---|---|---|---|---|---|
| 1 | 527.0 | 545.1 "M+H" | 546.1 "isotope" | 562.1 | 567.9 | 568.9 "M+H" | 569.9 | 579.0 "M+H" | 580.1 | 581.1 "isotope" | |
| | 583.0 "M+K" | 585.1 "M+Na" | 592.1 | 601.0 "M+Na M+K" | 607.0 "M+K" | 613.2 | 624.0 | 625.0 | 626.0 | 627.0 | |
| | 632.0 | 633.0 | 675.1 | 677.0 | 681.1 "M+H" | 682.0 "M+Na" | 698.0 "M+K" | 700.0 | 716.1 | 717.1 | |
| | 719.0 "M+K" | 761.0 | 817.1 | 852.1 | 853.1 "isotope" | | | | | | |
| 2 | 703.6 | 732.5 | ■734.6 "M+H" | 735.6 "isotope" | ■756.5 | 758.5 | | 761.6 "isotope" | 762.6 "M+H" | ■772.5 | |
| | ▲782.6 "M+Na" | 783.5 "isotope" | 784.6 "M+Na" | 786.6 | 787.6 | ▲788.6 | 789.6 | ●798.5 | 799.5 "M+K" | 800.5 | |
| | ●810.6 "M+Na" | ●826.5 "M+K" | 870.6 | 871.6 "isotope" | 895.6 "M+Na" | 896.6 "M+H" | 897.6 | 898.6 "M+H" | 899.6 "isotope" | ●918.6 | |
| 3 | 919.6 "M+Na" | 920.6 "M+Na" | 922.6 | 924.6 | □828.6 "M+Na" | 829.5 "isotope" | 830.5 "M+Na" | 832.5 | | | |
| | 851.5 | □806.6 "M+H" | 807.6 | 808.6 "M+H" | | □872.5 "M+K" | | | □834.6 "M+H" | 835.6 "M+H" | |
| | 836.6 | □844.5 "M+K" | □856.6 "M+Na" | 857.6 "M+Na" | 868.6 | 893.7 | 914.7 | 943.6 | 970.6 | 971.6 | |
| | 972.6 | 577.5 | 603.5 | 886.8 | 891.8 | | | 921.7 | 923.7 | 925.8 | |
| 4 | 575.5 | | | | | | | | | | |

MASS SPECTROMETRY DATA ANALYSIS METHOD AND ANALYSIS DEVICE

TECHNICAL FIELD

The present invention relates to a mass spectrometry data analysis method and analysis device for analyzing mass spectrometry imaging data collected by executing mass spectrometry on each of a plurality of micro areas within a two-dimensional region of a sample.

BACKGROUND ART

A device called a microscopic mass spectrometry device or an imaging mass spectrometry device has been developed as a device for performing morphological observations of a sample such as biological tissue and simultaneously measuring the distribution of substances (molecules) present in a prescribed region of the sample (see Non-Patent Literature 1 and the like). With such a device, it is possible to obtain a distribution image (mapping image) of ions having specific mass/charge ratios m/z contained in an arbitrary region of the sample designated based on microscopic observations while almost completely maintaining the form of the sample without grinding or pulverizing the sample. In particular, the application of obtaining distribution information of specific components such as proteins contained in cells in the body, for example, is highly anticipated in the fields of biochemistry, medicine/pharmacology, and the like.

In order to make it possible for an analyzer to easily grasp desired information related to a sample—for example, the types of substances characterizing the sample, their concentration distributions, and the like—in imaging mass spectrometry, it is important to perform appropriate analytical processing on the collected mass spectrometry imaging data and to display the results in an appropriate format. When mass spectrometry imaging data of a two-dimensional region of a certain amount of area of a sample is obtained, the data contains mass spectrum data of multiple measurement points (micro areas). Therefore, the quantity of data becomes enormous. A great amount of time and effort are required for a person to examine this enormous amount of data and extract significant information.

In order to grasp the mass/charge ratios expressing a specific distribution in a certain measurement region, the mass/charge ratios of analytical target peaks are typically first selected by executing peak detection on the mass spectrometry spectrum data (see Non-Patent Literature 2). One known example of a peak detection method is a method in which a number of peaks designated in order of decreasing signal intensity in the mass spectrum are extracted and the mass/charge ratios of these peaks are analyzed. In this method, peak detection dependent on signal intensity alone is performed, so peaks with a signal intensity exceeding a certain level are all selected without monoisotopic peaks or isotope peaks derived from the same substance being differentiated from one another. Therefore, even if a prescribed number of peaks are selected from the mass spectrum, isotope peaks derived from the same substance are, in actuality, often included (that is, the selected peaks are essentially redundant). In order to avoid this, it is necessary to identify monoisotopic peaks and isotope peaks derived from the same substance in the mass spectrum or to identify isotope peak groups to which a plurality of isotope peaks derived from the same substance belong.

The method described in Patent Literature 1 is a method for identifying both monoisotopic peaks and isotope peaks derived from the same substance in a mass spectrum in which both types of peaks are present. This is a method in which the intensity ratios of a plurality of isotope peaks presumed to belong to a single isotope peak group in an actually measured mass spectrum and the intensity ratios of isotope peaks calculated theoretically based on the natural isotope ratios and the like of each element are compared, and after an isotope peak group assessed to have matching intensity ratios is selected, monoisotopic ion peaks are selected from the peaks contained in the isotope peak group. However, this method fundamentally performs processing on a single mass spectrum. Therefore, when this method is used for the analysis of mass spectrometry imaging data, it is necessary to repeat the same processing for each mass spectrum obtained for a single micro area, and this processing itself takes an enormous amount of time. Moreover, since the obtained results (m/z values of peaks) are obtained by means of processing performed separately in each micro area, it is necessary to coordinate the results (m/z values) between each micro area in order to handle the results as imaging data, which is troublesome. Further, depending on the measurement conditions, the intensity ratios of a plurality of isotope peaks may not be as predicted theoretically, and in such cases this method cannot be applied.

The method described in Patent Literature 2 is a method for identifying monoisotopic peaks/isotope peaks confined to mass spectrometry imaging data. In this method, mapping images of isotope peak candidates selected based on the intensity ratios of peaks in a mass spectrum are respectively created, and the similarity of the mapping images is assessed to determine isotope clusters to which isotope peaks derived from the same substance belong and monoisotopic peaks contained therein. However, since it is difficult to assess the similarity of a plurality of mapping images automatically, the person in charge of analysis must perform the operation of visually assessing the similarity of the images, but such assessment involves differences among individuals, so it is difficult to maintain the stability or objectivity of the results.

(PATENT LITERATURE 1) Japanese Unexamined Patent Application Publication 2006-284305

(PATENT LITERATURE 2) International Patent Publication 2008/126151 Pamphlet

Non-Patent Literatures (NON-PATENT LITERATURE 1) Kiyoshi Ogawa and 5 others, "Development of a Microscopic Mass Spectrometry Device," Shimadzu Review, Shimadzu Corporation, published Mar. 31, 2006, Vol. 62, Nos. 3-4, p. 125-135

(NON-PATENT LITERATURE 2) Liam (Liam A. McDonnell) and 4 others, "Imaging Mass Spectrometry Data Reduction: Automated Feature Identification and Extraction," American Society for Mass Spectrometry, 2010, 21, p. 1969-1978

SUMMARY OF THE INVENTION

The present invention was conceived in order to solved the problem described above, and its purpose is to provide a mass spectrometry data analysis method and analysis device which, when finding the mass/charge ratios of analytical target peaks by executing peak detection on data collected by imaging mass spectrometry, is capable of selecting peaks by identifying monoisotopic peaks/isotope peaks derived from the same substance with high precision, regardless of the measurement conditions and without relying on the judgment of the person in charge of analysis or the like.

The first invention conceived in order to solve the problem described above is a mass spectrometry data analysis method for analyzing data collected by executing mass spectrometry over respectively prescribed mass/charge ratio ranges of a plurality of micro areas set in a two-dimensional region of a sample, the method comprising:

a) a peak detection step in which peak information including the intensities and mass/charge ratios of peaks is collected by executing peak detection processing on mass spectrum data obtained for each of the micro areas;

b) an intensity standardization step in which the peak information for each micro area obtained in the peak detection step is collected and the intensity values of each micro area are standardized so that the spatial intensity distributions can be compared for each mass/charge ratio for all of the peaks;

c) a clustering execution step in which the mass/charge ratios contained in the peak information are classified into a prescribed number of clusters by using the clustering of the spatial intensity distributions of each mass/charge ratio after standardization by the intensity standardization step; and d) an identification step in which the mass/charge ratios of ions derived from the same substance are identified using at least differences in a plurality of mass/charge ratios classified into the same cluster.

The mass spectrometry data analysis device of the second invention is a mass spectrometry data analysis device for implementing the mass spectrometry data analysis method of the first invention by means of analyzing data collected by executing mass spectrometry over respectively prescribed mass/charge ratio ranges of a plurality of micro areas set in a two-dimensional region of a sample, the device being provided with:

a) a peak detection means for collecting peak information containing the intensities and mass/charge ratios of peaks by executing peak detection processing on mass spectrum data obtained for each of the micro areas;

b) an intensity standardization means for collecting peak information for each micro area obtained by the peak detection means and standardizing the intensity values of each micro area so that the spatial intensity distributions can be compared for each mass/charge ratio for all of the peaks;

c) a clustering execution means for classifying the mass/charge ratios contained in the peak information into a prescribed number of clusters by using the clustering of the spatial intensity distributions of each mass/charge ratio after standardization by the intensity standardization means; and d) an identification means for identifying the mass/charge ratios of ions derived from the same substance using at least differences in a plurality of mass/charge ratios classified into the same cluster.

As one concrete mode of the mass spectrometry data analysis method of the first invention, in the identification step described above, it is possible to identify mass charge/ratios belonging to an isotope group derived from the same substance using differences in the mass/charge ratios and non-standardized intensity information for a plurality of mass/charge ratios classified into the same cluster and to select only a mass/charge ratio corresponding to a monoisotopic peak out of the plurality mass/charge ratios belonging to the same isotope group. That is, using the clustering of spatial intensity distributions for each mass/charge ratio, it is possible to identify peaks corresponding to monoisotopic ions containing only the main isotope (stable isotope with the greatest abundance ratio) of each element and peaks corresponding to isotope ions containing at least some isotopes other than the main isotope.

As another concrete mode of the mass spectrometry data analysis method of the first invention, in the identification step described above, it is possible to identify the mass/charge ratios corresponding to a plurality of adduct ion peaks derived from the same substance using differences in a plurality of mass/charge ratios classified into the same cluster and to select a mass/charge ratio corresponding to a single peak from among a plurality of adduct ion peaks derived from the same substance. An adduct ion is an ion to which a specific component such as an alkali method such as Na or K or ammonia is added to the target ion.

Since the natural abundance ratios of isotopes are determined for each element, although various ions which are derived from the same substance and differ only in the isotopes of their constituent elements have respectively differing absolute intensities, they demonstrate similar spatial intensity distributions. Therefore, when the intensity values of each micro area are standardized, the effects of the absolute values of the intensities in the spatial intensity distributions are eliminated, so the distances described in the clustering technique become smaller in spatial intensity distributions which differ only in the isotopes derived from the same substance or differ in mass/charge ratios due to the addition of other components. As a result, when clustering is executed in the clustering execution step, the probability that spatial intensity distributions of different mass/charge ratios derived from the same substance will be classified as the same cluster becomes higher, which makes it possible to identify monoisotopic ions and isotope ions derived from the same substance, for example, in the identification step.

If the number of clusters is too small when clustering is executed in the clustering execution step, the number of mass/charge ratios placed in a single cluster becomes too large, which leads to a decrease in the identification precision of ions derived from the same substance. On the other hand, if the number of clusters is too large, the likelihood that spatial intensity distributions of ions derived from the same substance will be placed in different clusters increases, which also leads to a decrease in the identification precision. To address such a problem, rather than designating the number of clusters in advance, the optimal or nearly optimal number of clusters should be determined automatically using analysis of variance, for example, when executing clustering in the clustering execution step.

With the mass spectrometry data analysis method and analysis device of the present invention, as described above, the effects of the absolute intensities of the spatial intensity distribution of each mass/charge ratio are eliminated, so it is possible to select a target monoisotopic peak by identifying monoisotopic ions and isotope ions derived from the same substance with high precision and to select one out of a plurality of adduct peaks derived from the same substance at high precision, even for data obtained under measurement conditions in which the intensity ratios of isotope ions are not as predicted theoretically. Moreover, whereas conventionally there are often cases in which special preprocessing is performed to prevent the generation of unnecessary adduct ions when performing mass spectrometry on a biological sample, with the present invention unnecessary adduct ion peaks are eliminated without performing such preprocessing, which saves the trouble associated with preprocessing.

Further, with the mass spectrometry data analysis device and the mass spectrometry data analysis method of the present invention, it is not necessary for the person in charge of analysis to visually compare or assess the spatial intensity distribution for each mass/charge ratio, and this yields the advantage that high throughput can be realized, whereby the burden on the person in charge of analysis is alleviated and highly stable and accurate monoisotopic peak/isotope peak identification can be formed without dependence on the experience or technical ability of the person in charge of analysis.

BRIEF DESCRIPTION OF THE DRAWINGS

The patent or application file contains at least one drawing executed in color. Copies of this patent or patent application publication with color drawing(s) will be provided by the Office upon request and payment of necessary fee.

DETAILED DESCRIPTION OF THE EXEMPLARY EMBODIMENTS

Figure 1:
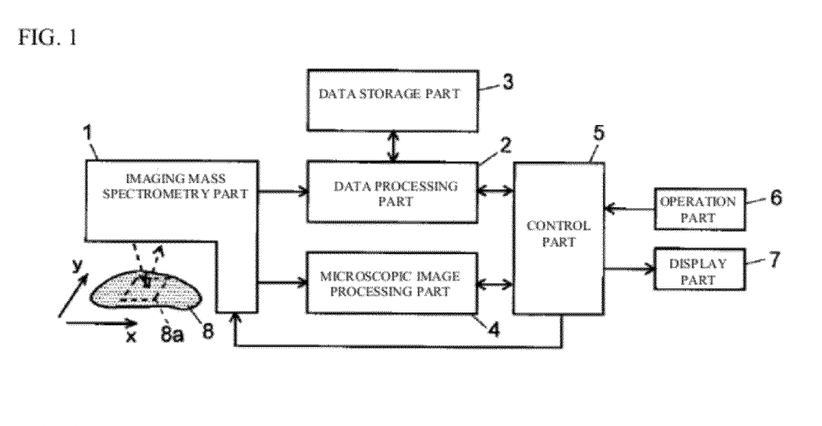
FIG. 1 is a schematic block diagram of an embodiment of an imaging mass spectrometry device using the mass spectrometry data analysis device of the present invention.

An embodiment of an imaging mass spectrometry device using the mass spectrometry data analysis device of the present invention will be described hereinafter with reference to the attached drawings. FIG. 1 is a schematic block diagram of the imaging mass spectrometry device of this embodiment.

This imaging mass spectrometry device is provided with an imaging mass spectrometry main body 1 for performing microscopic observations of a two-dimensional measurement region 8a of a sample 8 and executing imaging mass spectrometry in the region 8a, a data processing part 2 for performing analysis processing on mass spectrometry spectrum data collected by the imaging mass spectrometry main body 1, a data storage part 3 for storing mass spectrometry spectrum data, a microscopic image processing part 4 for forming microscopic images by processing image signals captured by the imaging mass spectrometry main body 1, a control part 5 for controlling each of these parts, and an operation part 6 and a display part 7 connected to the control part 5.

As described in Non-Patent Literature 1 and the like, the imaging mass spectrometry main body 1 includes a MALDI ion source, an ion transport optical system, an ion trap, a time-of-flight mass spectrometer, and the like, and it executes mass spectrometry over a prescribed mass/charge ratio range for micro areas of a prescribed size. Although not shown in the drawing, the imaging mass spectrometry main body 1 includes a driving part which moves a stage on which the sample 8 is placed with high precision in the two mutually orthogonal axial directions of the x-direction and the y-direction, and the collection of mass spectrometry spectrum data for an arbitrary two-dimensional measurement region 8a can be achieved by executing mass spectrometry over the prescribed mass/charge ratio ranges each time the sample 8 is moved with a prescribed step width. At least some of the functions of the data processing part 2, the data storage part 3, the microscopic image processing part 4, the control part 5, and the like are achieved by executing dedicated processing/control software loaded into a personal computer.

Figure 2:
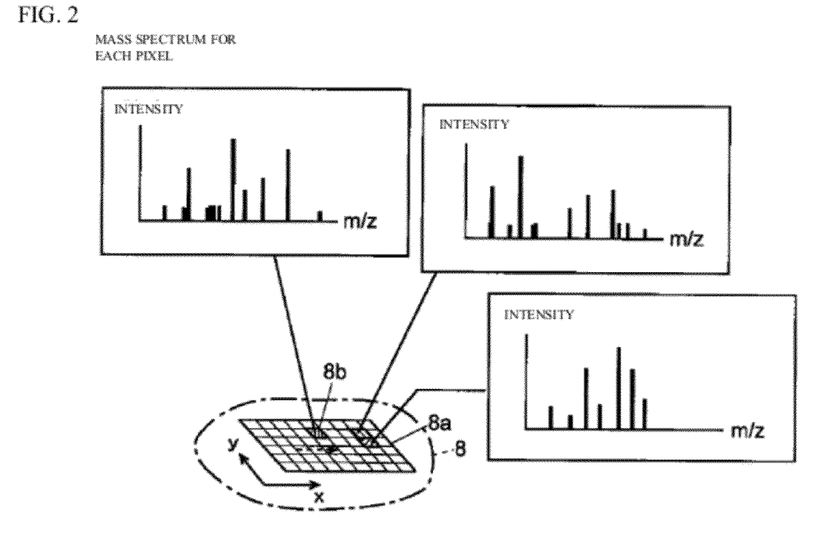
FIG. 2 is a schematic block diagram of the mass spectrum data collection operation in the imaging mass spectrometry device of this embodiment.
Figure 3:
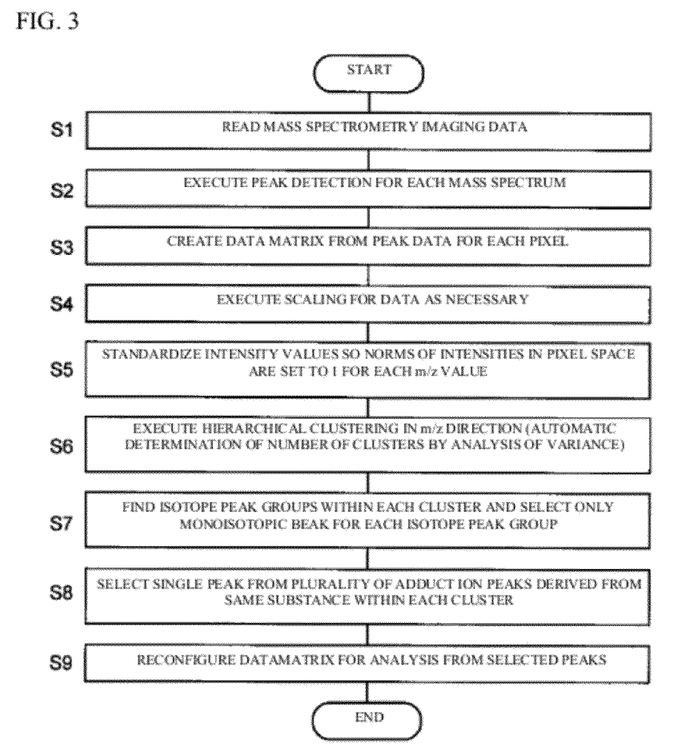
FIG. 3 is a flowchart of the characteristic data analysis operation of the imaging mass spectrometry device of this embodiment.

The imaging mass spectrometry device of this embodiment is characterized by the data analysis processing of the data processing part 2 which performs analysis processing on an enormous amount of mass spectrometry spectrum data collected by the imaging mass spectrometry main body 1 and displays it on the screen of the display part 7. An example of this characteristic data analysis processing will be described in detail using FIGS. 2 and 3. FIG. 2 is a schematic block diagram of the mass spectrum data collection operation of the imaging mass spectrometry device of this embodiment, and FIG. 3 is a flowchart showing the characteristic data analysis procedure of the imaging mass spectrometry device of this embodiment.

In the imaging mass spectrometry main body 1, as shown in FIG. 2, mass spectrum data is obtained for each of the micro areas 8b determined by finely dividing the inside of the prescribed two-dimensional measurement region 8a set in the sample 8 in the x-direction and the y-direction, respectively. This mass spectrum data constitutes the mass spectrum showing intensity signals over a prescribed mass/charge ratio range. The micro areas 8b need not be established densely inside the entire two-dimensional measurement region 8a as shown in FIG. 2, and they may be instead distributed sparsely, for example.

The length of one side of each of the micro areas 8b is ordinarily determined by the movement step width of the stage on which the sample 8 is placed. In mapping images showing the spatial intensity distributions in certain mass/charge ratios described below, the display colors in two-dimensional color display images are determined for each micro area 8b. Therefore, this micro area becomes the smallest unit of image processing such as coloration, so a pixel and a micro area are synonymous in image processing, and in this explanation a micro area will be called a pixel. That is, as shown in FIG. 2, pixels are arranged in a grid inside the two-dimensional measurement region 8a.

When the initiation of data analysis process is indicated in the state in which the mass spectrometry imaging data for the two-dimensional measurement region 8a (in this explanation, this is mass spectrum data for each pixel, but it may also be $MS^n$ spectrum data such as $MS^2$ spectrum data) is stored in the data storage part 3, the data processing part 2 first reads the mass spectrometry imaging data to be processed from the data storage part 3 (step S1) and extracts significant peaks by executing peak detection processing for each mass spectrum—that is, for each piece of data for each pixel (step S2). Specifically, a prescribed number of peaks are selected sequentially from peaks with higher signal intensity, for example, for each mass spectrum. As a result, noise peaks with small signal intensities are removed. The peak detection method is not limited to this example, and it is also possible to add processing in which peaks of specific m/z values or a specific m/z range designated in advance, for example, are excluded from selection, even if the signal intensities are high, or in which, conversely, peaks of specific m/z values or a specific m/z range designated in advance are selected, even if the signal intensities are low.

Figure 5:
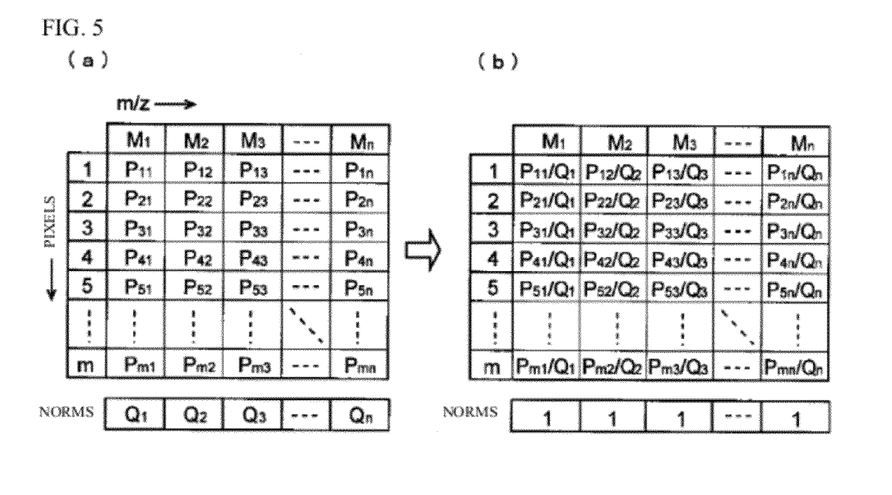
FIG. 5 is an explanatory diagram of norm standardization for each m/z value.

The data obtained by performing peak detection for each pixel as described above—that is, the peak information—represents the m/z values and the intensities of the peaks. Therefore, this data is organized in a data matrix format in which the pixel number is assigned to the vertical direction, the m/z value is assigned to the horizontal direction, and each term is defined as the intensity value of a peak (step S3). Of course, the rows and columns may be interchanged. FIG. 5(*a*) is an example of a data matrix. In this figure, $M_1, M_2, \ldots$ are m/z values, and $P_{11}, P_{12}, \ldots$ are peak intensity values.

Next, scaling is performed as necessary for the data of the data matrix (step S4). Scaling is performed to ensure that, if there is data with extremely large intensities, for example, the analysis is not dominated by this data. A specific example of a screening technique is one in which, in order to ensure that the mean value and standard deviation are reflected in the data, the mean value of all of the intensity values is first calculated and subtracted from each intensity value (that is, mean centering is performed), and the value is then divided by the variance (standard deviation) of the intensity values. However, Pareto scaling is typically more advantageous for the data of mass spectrum peaks. In Pareto scaling, after mean centering is performed, the value is divided by the square root of the variance.

Next, the intensity values are standardized for the data in the data matrix that has been scaled or has not been scaled as a norm of the intensities of the pixel spaces for each m/z value (that is, the norm of each row of the data matrix is set to 1) (step S5).

Figure 4:
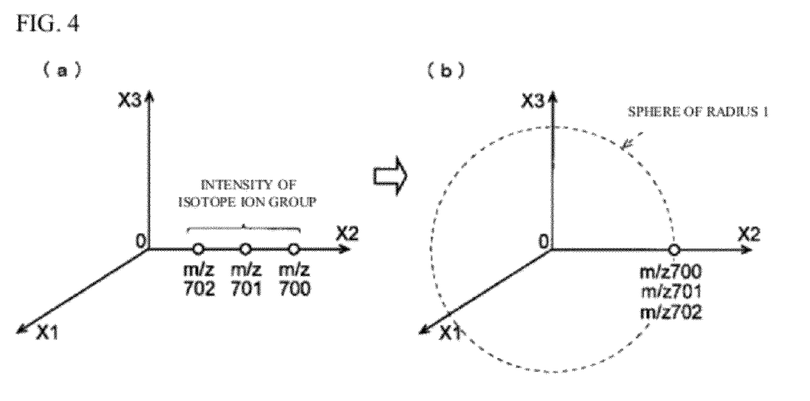
FIG. 4 is an explanatory diagram of norm standardization in pixel space.

FIG. 4 is a drawing showing the concept of norm standardization of the intensities of a pixel space. FIG. 4 shows the plot points of the three isotope ions m/z 700, m/z 701, and m/z 702 present in the pixel X2 in a pixel space with the intensities of the three pixels X1, X2, and X3 plotted on three axes, wherein (a) shows the points before standardization and (b) shows the points after standardization. In the state before standardization, as shown in FIG. 4(*a*), the plot points corresponding to the three isotope ions m/z 700, m/z 701, and m/z 702 of different intensities are present at different positions on the X2 axis. Setting the norm of the intensities of a pixel space to 1 means that the intensity at each plot point is divided by itself. Therefore, after standardization, as shown in FIG. 4(*b*), the plot points corresponding to the three isotope ions m/z 700, m/z 701, and m/z 702 of [different intensities] overlap at the same point on the X2 axis. Any plot point in the pixel space is positioned in a spherical shape with a radius of 1.

Specifically, in the data matrix shown in FIG. 5(*a*), one column in the vertical direction represents the intensity values of the pixel space for specific m/z values, so the norms of this vertical direction are respectively found (in this example, $Q_1, Q_2, \ldots$), and each intensity value is divided by the norm found above for each m/z value (see FIG. 5(*b*)). As a result, all of the intensity values are standardized so that the norm is 1 for each m/z value.

Next, the m/z values or spatial intensity distributions for each m/z value (that is, the data aggregate for each column of the data matrix) are classified into a plurality of clusters by performing hierarchical clustering (HCA) in the m/z direction for the data matrix standardized so that the norm is 1 for each m/z value as described above (step S6). At this time, the number of clusters is not set in advance but is instead determined automatically by one of various known techniques such as analysis of variance, for example, which eliminates the need for the person in charge of analysis or the like to input settings from an external device.

Although the respective absolute intensities differ in the spatial intensity distributions of the m/z values of peaks belonging to an isotope peak group (a plurality of peaks derived from ions which are generated from the same substance and differ only in the isotopes of the constituent elements), they all demonstrate similar spatial distributions. Standardizing each intensity value so that the norm is 1 (or another prescribed value) in the data matrix means that the spatial intensity distributions can be compared by eliminating the effects of the absolute values of the intensities. Therefore, the distance between isotope peaks (for example, the distance used in hierarchical clustering such as Euclid's distance, for example) becomes smaller than before standardization as a result of the standardization processing in step S5, so the likelihood of being placed together in the same cluster in hierarchical clustering increases. As a result, the m/z values of peaks having similar spatial intensity distributions, including the isotope peak group, are placed together in the same cluster.

In mass spectrometry, adduct ions in which various components are added to the ions in the ionization process of a target molecule are generated, but although the spatial intensity distributions of the m/z values of such adduct ion peaks also differ in their absolute intensities, they all demonstrate similar spatial distributions. Therefore, executing hierarchical clustering after the standardization described above allows m/z values of adduct ion peaks derived from the same substance but having different m/z values to be placed together in the same cluster with high probability.

Figure 6:
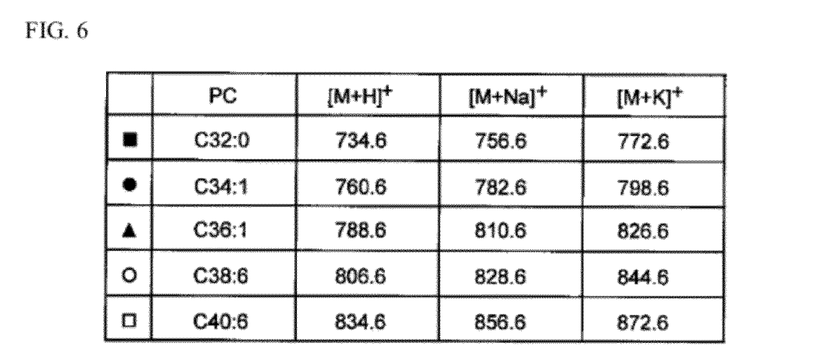
(FIG. 6) is an example of peaks derived from phospholipids extracted from mass spectrum data obtained using a mouse retina as a sample.

Here, an actual example of a case in which the data processing shown in FIG. 3 is applied to mass spectrometry imaging data collected using a mouse retina segment as a sample will be given. A maximum intensity mass spectrum was created by finding the maximum intensity for each m/z value in the entire region to be measured from this mass spectrometry imaging data, and when 100 peaks with the highest intensity were detected from this mass spectrum, considered to be the five types of phospholipids shown in FIG. 6 were selected. As shown in FIG. 6, in addition to proton-added ions ($(M+H)^+$) of these five types, ions considered to be sodium-added ions and potassium-added ions from the differences in mass/charge ratios were also respectively observed.

Figure 7:
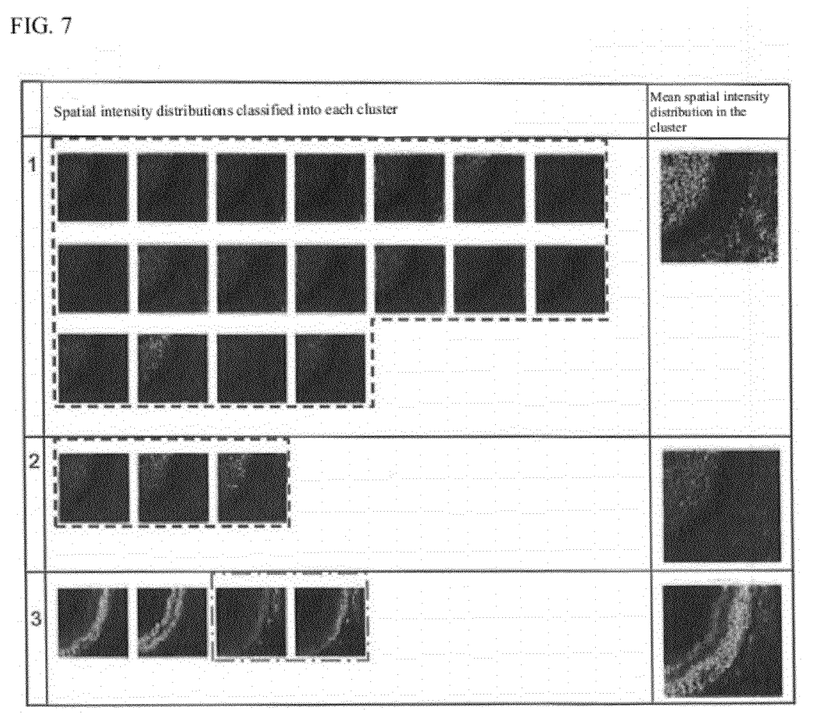
FIG. 7 is a diagram showing the spatial intensity distributions classified into each cluster and the mean spatial intensity distribution in each cluster when HCA was attempted without the standardization of data.
Figure 8:
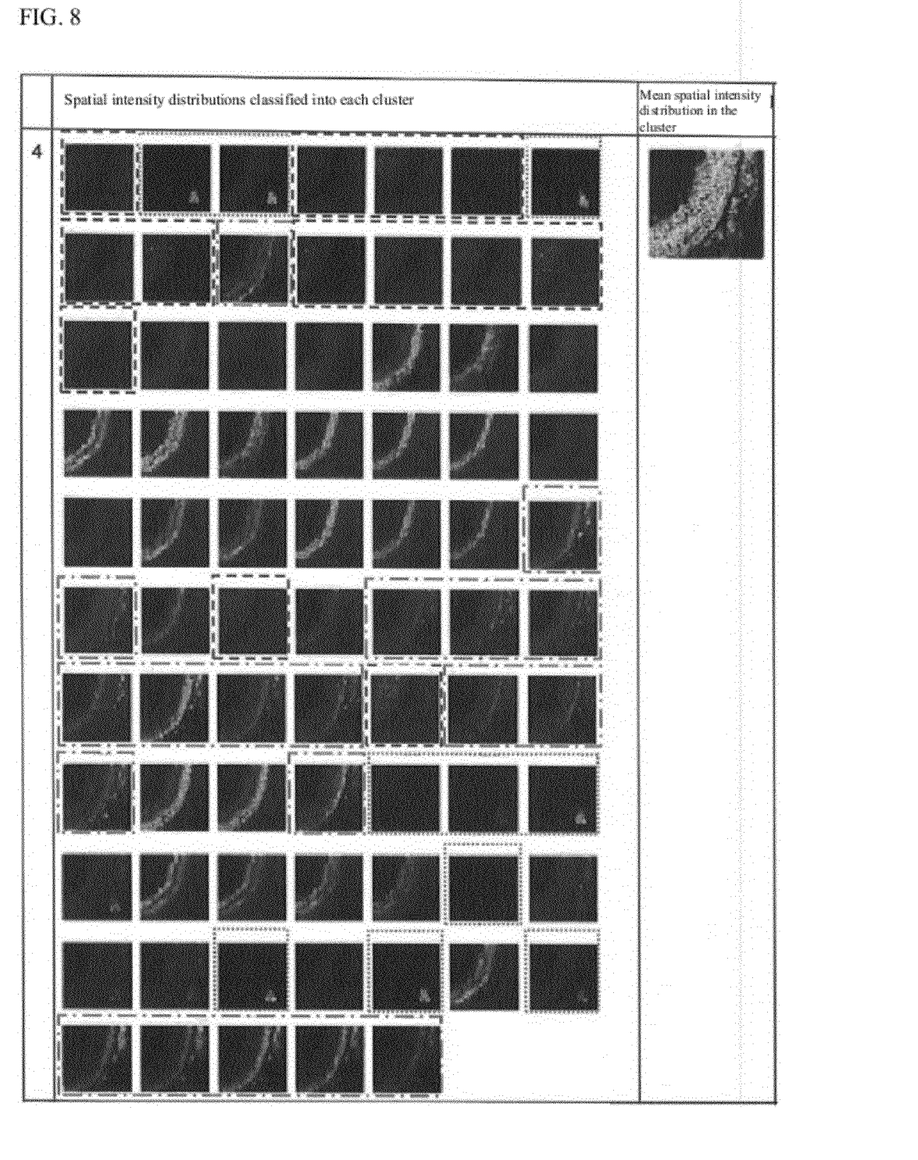
FIG. 8 is a diagram showing the spatial intensity distributions classified into each cluster and the mean spatial intensity distribution in each cluster when HCA was attempted without the standardization of data.

A data matrix was created defining the m/z values of the peaks detected as described above as the m/z values M1, M2, ... shown in FIG. 5(*a*), and the hierarchical clustering of step S6 was executed without performing the standardization processing of step S5. In hierarchical clustering, the distance between each peak was used as Euclid's distance of standardization, and the distance between clusters was based on the definition according to Ward's method. In this case, the optimal number of clusters assessed based on the inconsistency coefficient was 4, and all of the m/z values were classified into one of four clusters. FIGS. 7 and 8 are diagrams showing the spatial intensity distribution images (mapping images) and the mean spatial intensity distribution in each cluster corresponding to the m/z values classified into each cluster (1)-(4) at this time. As can be seen from FIG. 7, the spatial intensity distribution images contained in clusters (1) and (2) are divided into two clusters in spite of being quite similar. Conversely, in cluster (3) or (4), spatial intensity distribution images tending to be quite different are classified into the same cluster.

Figure 9:
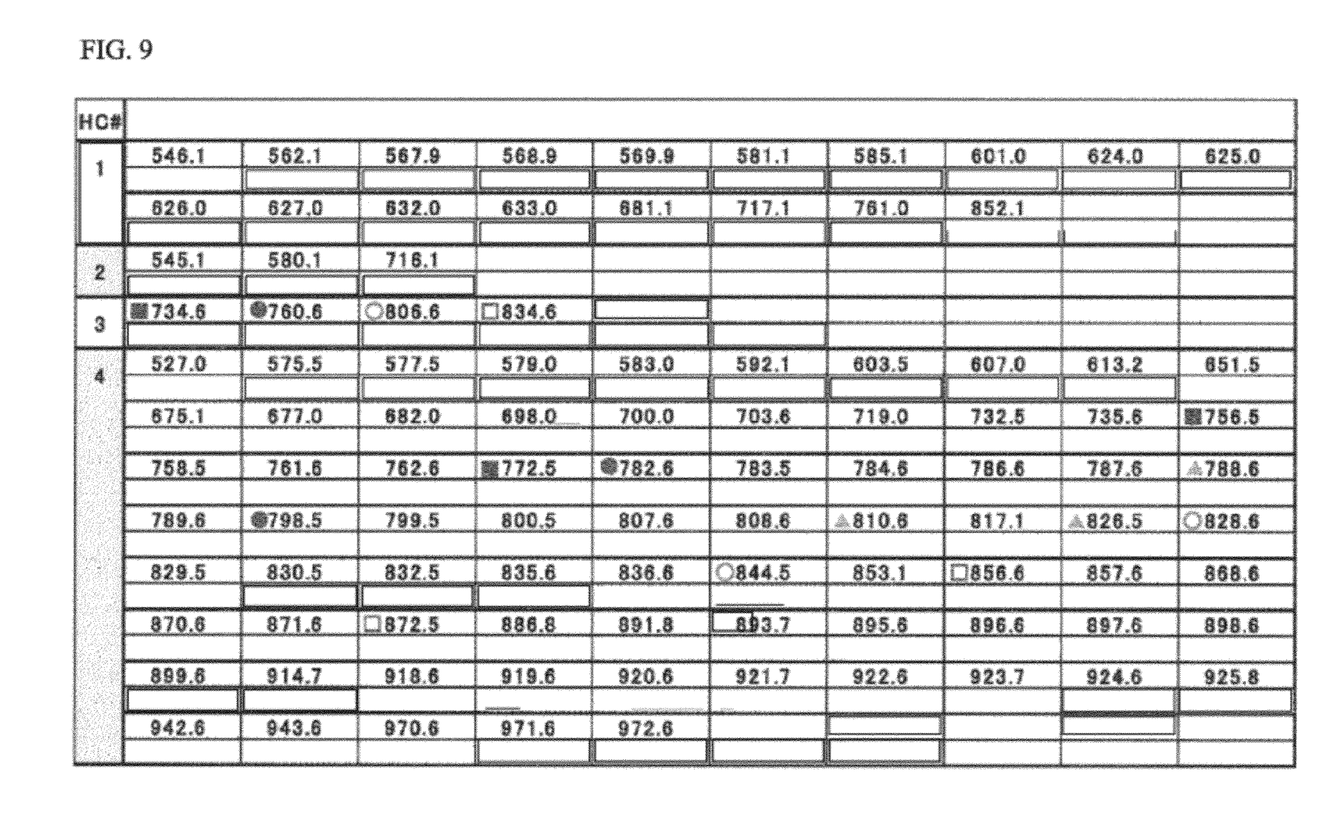
FIG. 9 is a diagram showing the results of peak detection in each cluster when HCA was attempted without the standardization of data.

FIG. 9 is a diagram showing the results of peak identification based on the results of the clustering shown in FIGS. 7 and 8. In FIG. 9, the m/z values indicated by symbols such as ○ marks correspond to ion peaks derived from the phospholipids shown in FIG. 6. Focusing attention on the ion peaks derived from these five types of phospholipids, the peaks are classified into different clusters in spite of being derived from the same substances. It can be seen from this results that, in hierarchical clustering omitting the processing of step S5, an isotope peak group or adduct ion peaks derived from the same substance are not consolidated into the same cluster, and accurate results cannot be obtained from these clustering results even by performing subsequent isotope ion/adduct ion identification processing.

Figure 10:
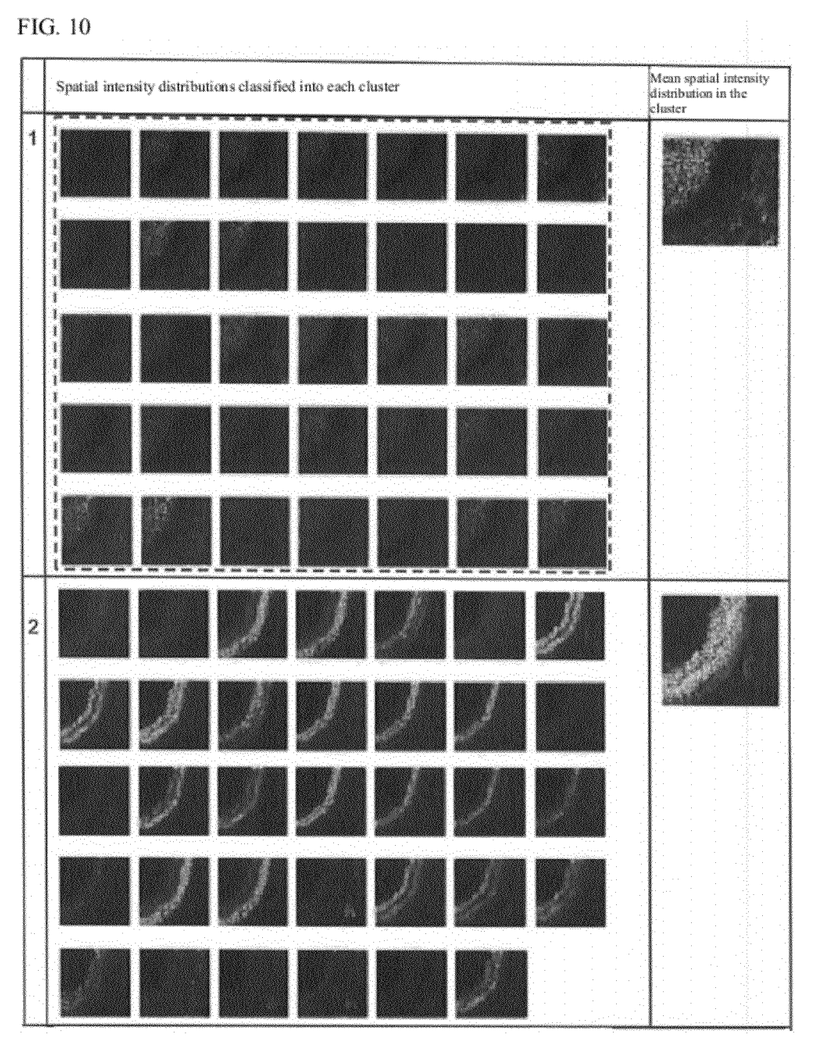
FIG. 10 is a diagram showing the spatial intensity distributions classified into each cluster and the mean spatial intensity distribution in each cluster when HCA was attempted after the standardization of data.
Figure 11:
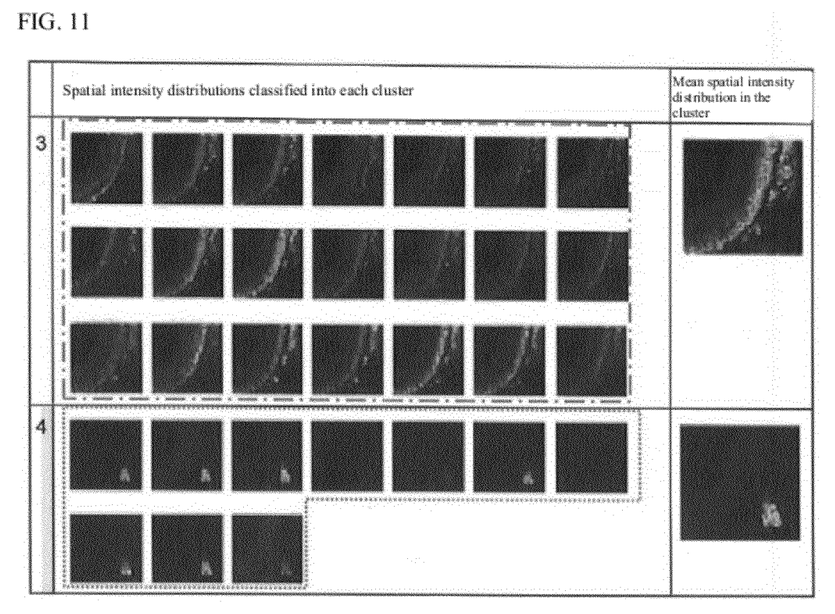
FIG. 11 is a diagram showing the spatial intensity distributions classified into each cluster and the mean spatial intensity distribution in each cluster when HCA was attempted after the standardization of data.

On the other hand, FIGS. 10 and 11 are diagrams showing the spatial intensity distribution images and the mean spatial intensity distribution in each cluster corresponding to the m/z values classified into each cluster (1)-(4) in the case in which the hierarchical clustering of step S6 was performed after the standardization processing of step S5 was performed. It can be seen from FIGS. 10 and 11 that m/z values with similar spatial intensity distributions are consolidated into the same clusters and that the differences of trends in the spatial intensity distributions are marked for each cluster. From these results alone, it can be interpreted that the likelihood of isotope ion or adduct ion peaks derived from the same substance being included in the same cluster is high.

Continuing this explanation by returning to FIG. 3, after all of the m/z values of the data matrix are classified into a plurality of clusters as described above, isotope peak groups are found within each cluster. Specifically, if the valence of ions is 1, the difference between the mass/charge ratios of isotope ions is 1 Da, so it is investigated whether there are m/z values with a difference of approximately 1 Da within the same cluster. If there are such m/z values, they are considered isotope peak group candidates, and the smallest m/z value among these values is considered a monoisotopic peak candidate. However, since it is possible that the difference between the m/z values of ions derived from completely different substances could coincidentally be around 1 Da, information regarding intensity ratios is used to confirm whether the candidates described above are actually an isotope peak group. Specifically, the theoretical isotope peak intensity ratio is calculated from the peak intensities of the monoisotopic candidates within the peaks included in an isotope peak group based on the natural abundance ratios of the isotopes, and it is assessed whether they can be considered a true isotope peak group by comparing this theoretical ratio to the intensity ratios of the actual isotope peak group candidates. If they are assessed to be an actual isotope peak group, only the m/z value corresponding to the monoisotopic peak is kept, and the other isotope peak information is deleted. On the other hand, if a peak group of m/z values of approximately 1 Da is not an isotope peak group, all of the peak information is kept without being deleted (step S7).

Figure 12:
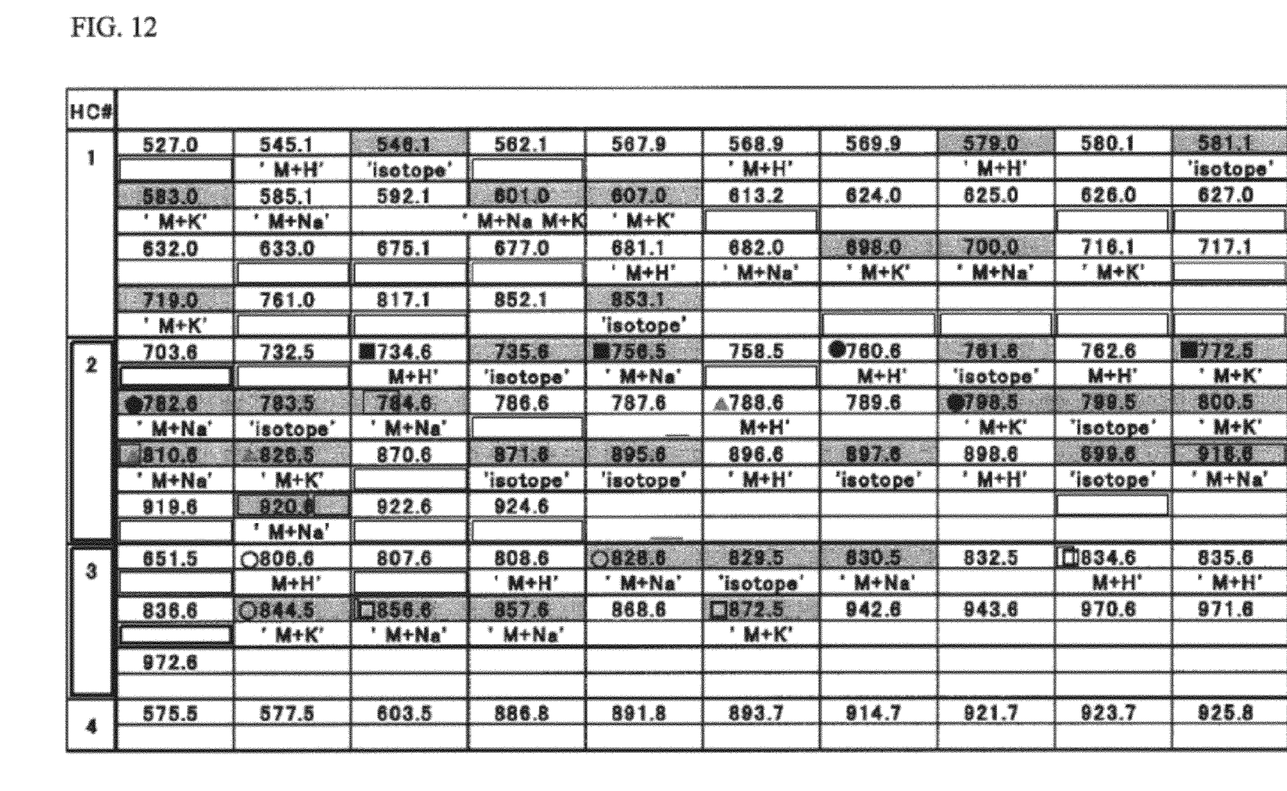
FIG. 12 is a diagram showing the results of peak detection in each cluster when HCA was attempted after the standardization of data.

FIG. 12 is a diagram showing the results of peak identification based on the results of the clustering shown in FIGS. 10 and 11. In FIG. 12, the m/z values in the cells with shaded backgrounds indicate peaks removed by the processing described above. The m/z values indicated by symbols such as ○ marks correspond to ion peaks derived from the phospholipids shown in FIG. 6. If peaks are assessed to be isotope peaks, "isotopic" is included under the m/z values, whereas if they are assessed to be adduct ion peaks, "M+H+," "M+Na," and "M+K" are respectively included under the respective m/z values. It can be seen from FIG. 12 that if there are isotope ions, the monoisotopic peak is kept and all other peaks are deleted. Information for singular peaks not constituting an isotope peak group are kept as they are without being deleted.

As an example of a method for calculating the intensities of isotope peaks, the Averagine model, which is conventionally used to calculate the elemental composition of amino acid sequences, may be used. The details of the Averagine model are disclosed, for example, in the following publication: Senko (Michel W. Senko) et al., "Determination of monoisotopic masses and ion populations for large biomolecules from resolved isotopic distributions", Journal of American Soc. Mass Spectom., 6, 1995, pp. 229-233.

Next, peak pairs corresponding to the differences in the mass/charge ratios of known adduct ions are found for the peaks in each cluster left behind as a result of the processing of step S7, and these are considered candidates for an adduct ion peak group derived from the same substance. The peak with the largest mean intensity in all of the measurement regions is kept as a single representative peak, and all other adduct ion peak information is deleted (step S8). It can be seen from the results of FIG. 12 that since adduct ion peaks of the five types of phospholipids shown in FIG. 6 are consolidated into the same cluster as a result of hierarchical clustering, adduct ion peaks can be identified precisely by differences in the mass/charge ratios.

Once peaks (m/z values) which are derived from the same substance and can be considered to be redundant are removed through steps S7 and S8, the peaks of each of the remaining clusters are consolidated, and a data matrix of the same format as that created in step S3 is reconfigured from this peak information (step S9). As a result, a data matrix with a reduced amount of information can be obtained by deleting peak information which is not useful for analysis such as isotope peaks or adduct ion peaks, so it becomes possible to obtain mapping images of m/z values indicating specific distributions, for example, with high precision based on the reconfigured data matrix.

Figure 13A:
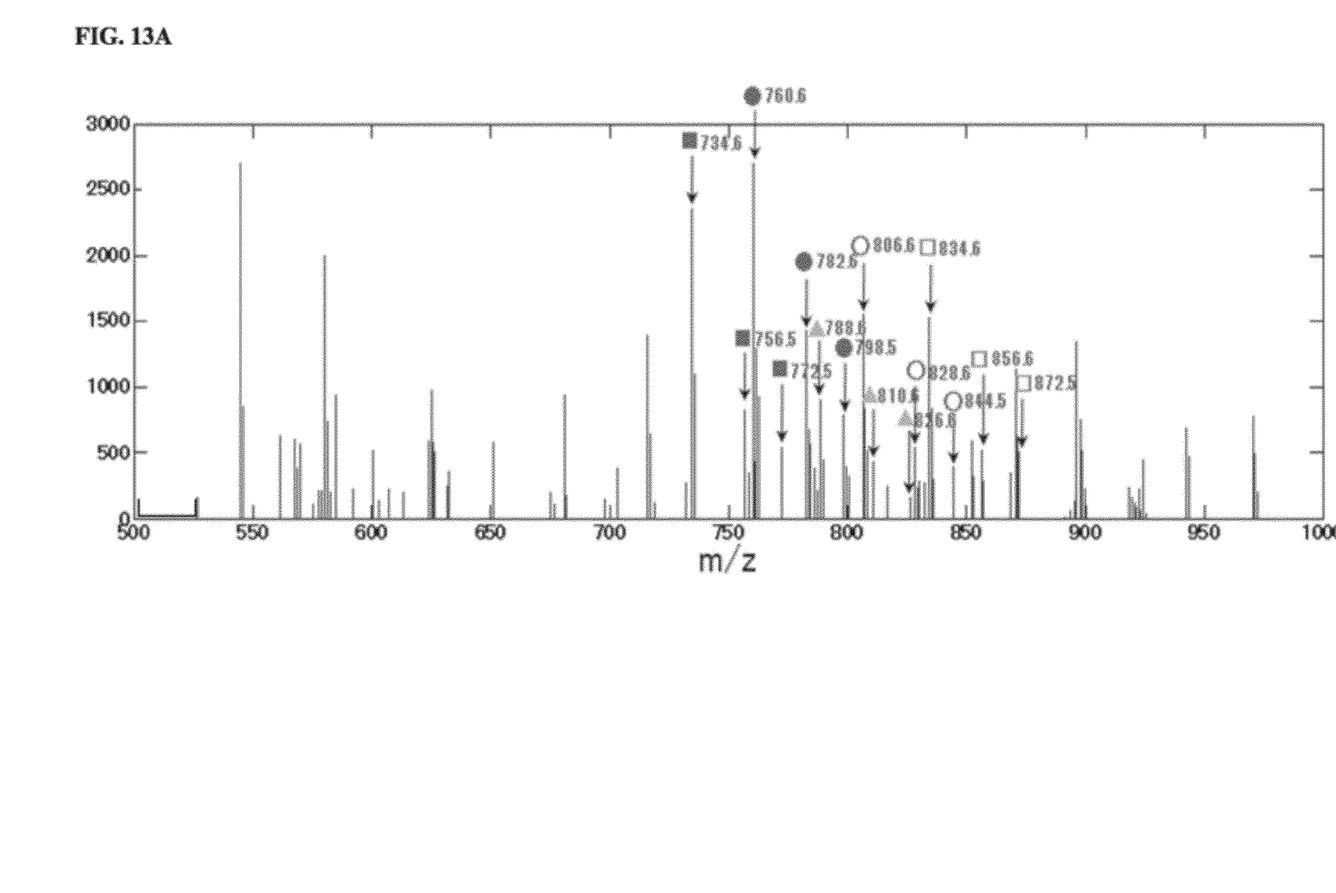
FIG. 13 is a diagram showing the mean mass spectrums before and after the application of peak identification/removal processing according to the present invention.
Figure 13B:
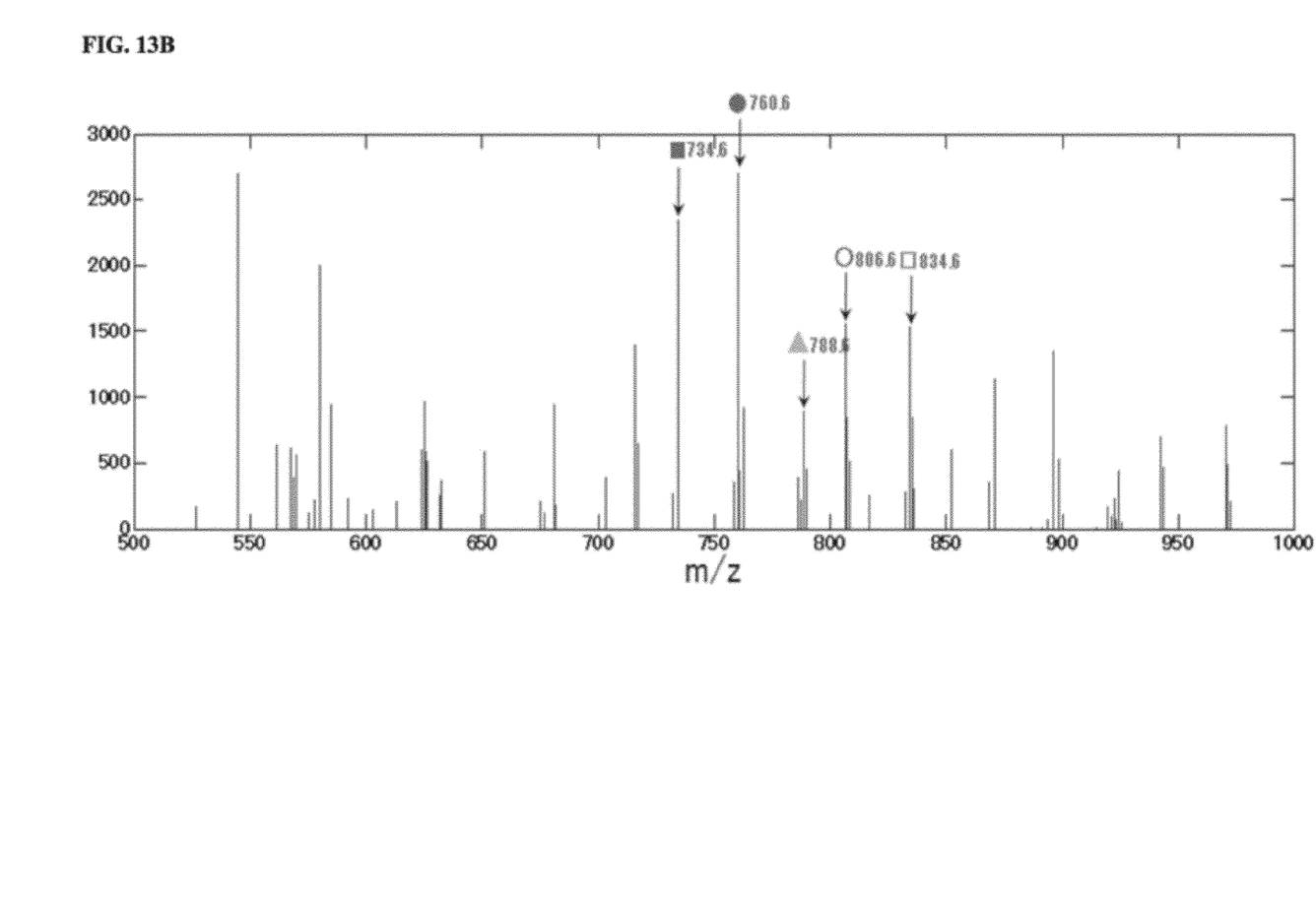

FIG. 13 is a mean mass spectrum of this example, wherein (a) is the state prior to the execution of the isotope ion/adduct ion peak removal processing described above, and (b) is the state after the execution of isotope ion/adduct ion peak removal processing. The m/z values indicated by symbols such as ○ marks in the diagrams correspond to ion peaks derived from the phospholipids shown in FIG. 6. It can be confirmed from FIG. 13 that all peaks except those with the greatest mean intensities have been eliminated in each of the adduct ion peaks derived from the five types of phospholipids shown in FIG. 6. In this example, 35 out of 100 peaks are eliminated by the isotope ion/adduct ion peak removal processing described above.

The embodiment described above is merely one example of the present invention, and it goes without saying that appropriate variations, modifications, and additions within the scope of the gist of the present invention are also included in the scope of the patent claims of this application. For example, in the embodiment described above, hierarchical clustering was executed as a form of clustering, but non-hierarchical clustering may also be used.

EXPLANATION OF REFERENCES

1 ... imaging mass spectrometry main body
2 ... data processing part
3 ... data storage part
4 ... microscopic image processing part
5 ... control part
6 ... operation part
7 ... display part
8 ... sample
8$a$ ... two-dimensional measurement region
8$b$ ... micro area (pixel)

What is claimed is:

1. A mass spectrometry data analysis method for analyzing data collected by executing mass spectrometry on each of a plurality of micro areas set in a two-dimensional region of a sample by a mass spectrometry device, the method comprising:
   a) a peak detection step in which peak information including the intensities and mass/charge ratios of peaks is collected by executing peak detection processing on mass spectrum data obtained for each of said plurality of micro areas by a processor;
   b) an intensity standardization step in which the peak information for each micro area obtained in said peak detection step is collected and the intensity values of each micro area are standardized so that the spatial intensity distributions can be compared for each mass/charge ratio for all of the peaks by the processor;
   c) a clustering execution step in which the mass/charge ratios that are made to correspond to the spatial intensity distributions are classified into a prescribed number of clusters by using the clustering of the spatial intensity distributions of each mass/charge ratio after standardization by said intensity standardization step by the processor; and
   d) an identification step in which the mass/charge ratios of ions derived from the same substance are identified using at least differences in a plurality of mass/charge ratios classified into the same cluster by the processor.

2. A mass spectrometry data analysis method according to claim 1;
   wherein, in said identification step, peaks belonging to an isotope group derived from the same substance are identified using differences in a plurality of mass/charge ratios classified into the same cluster and non-standardized intensity information, and only a monoisotopic peak is selected from the peaks belonging to the same isotope group.

3. A mass spectrometry data analysis method according to claim 2;
   wherein, in said identification step, a plurality of adduct ion peaks derived from the same substance are further identified using differences in a plurality of mass/charge ratios classified into the same cluster, and one peak is selected from the plurality of adduct ion peaks derived from the same substance.

4. A mass spectrometry data analysis device for analyzing data collected by executing mass spectrometry on each of a plurality of micro areas set in a two-dimensional region of a sample, the device being provided with:
   a) a peak detection collector that collects peak information containing the intensities and mass/charge ratios of peaks by executing peak detection processing on mass spectrum data obtained for each of said micro areas;
   b) an intensity standardization collector that collects peak information for each micro area obtained by said peak detection means and standardizing the intensity values of each micro area so that the spatial intensity distributions can be compared for each mass/charge ratio for all of the peaks;
   c) a clustering execution classifier that classifies the mass/charge ratios that are made to correspond to the spatial intensity distributions into a prescribed number of clusters by using the clustering of the spatial intensity distributions of each mass/charge ratio after standardization by said intensity standardization means; and
   d) an identifier that identifies the mass/charge ratios of ions derived from the same substance using at least differences in a plurality of mass/charge ratios classified into the same cluster.

5. A mass spectrometry data analysis device according to claim 4;
   wherein said identifier identifies peaks belonging to an isotope group derived from the same substance but having different mass/charge ratios using differences in the mass/charge ratios of a plurality of spatial intensity distributions classified into the same cluster and non-standardized intensity information and selects only a monoisotopic peak from the same isotope group.

6. A mass spectrometry data analysis device according to claim 5;
   wherein said identifier further identifies a plurality of adduct ion peaks derived from the same substance using differences in the mass/charge ratios of a plurality of spatial intensity distributions classified into the same cluster and selects only one of the plurality of adduct ion peaks derived from the same substance.

* * * * *